US00PP30374P2

(12) United States Plant Patent
Menzel

(10) Patent No.: US PP30,374 P2
(45) Date of Patent: Apr. 9, 2019

(54) ***MISCANTHUS* PLANT NAMED 'FIRE DRAGON'**

(50) Latin Name: *Miscanthus sinensis*
Varietal Denomination: Fire Dragon

(71) Applicant: Klaus Menzel, Woellstein (DE)

(72) Inventor: Klaus Menzel, Woellstein (DE)

( * ) Notice: Subject to any disclaimer, the term of this patent is extended or adjusted under 35 U.S.C. 154(b) by 0 days.

(21) Appl. No.: 15/932,744

(22) Filed: Apr. 18, 2018

(51) Int. Cl.
*A01H 5/12* (2018.01)

(52) U.S. Cl.
USPC ..... Plt./384

(58) Field of Classification Search
USPC ..... Plt./384
See application file for complete search history.

*Primary Examiner* — Susan McCormick Ewoldt
*Assistant Examiner* — Karen M Redden
(74) *Attorney, Agent, or Firm* — Bethany R. Roahrig; Cochran Freund & Young LLC

(57) ABSTRACT

A new and distinct cultivar of *Miscanthus* plant named 'Fire Dragon' that is characterized by an upright plant habit, arching foliage which turns intense orange-red in October, and flowers which are silky silver-white in appearance, is disclosed. In combination, these traits set 'Fire Dragon' apart from all other existing varieties of *Miscanthus* known to the inventor.

1 Drawing Sheet

Genus and species: *Miscanthus sinensis.*
Variety denomination: 'Fire Dragon'.

BACKGROUND OF THE NEW PLANT

The present invention relates to a new and distinct cultivar of *Miscanthus*, also known as Maiden Grass, which is grown as an ornamental plant for use in the garden and landscape. The new cultivar is known botanically as *Miscanthus sinensis* and will be referred to hereinafter by the cultivar name 'Fire Dragon'. The genus *Miscanthus* is included in the plant family Poaccac.

'Fire Dragon' was discovered in 1992 as an open-pollinated seedling which was growing in the inventor's garden in Woellstein, Germany. At that time, the inventor had established two varieties of *Miscanthus* in his garden, namely *Miscanthus sinensis* 'Rotsilber' (unpatented) and *Miscanthus sinensis* 'Yakushima Dwarf' (unpatented). The inventor considers that these two varieties are the parents of the open-pollinated seedling, 'Fire Dragon'.

The inventor observed that the new variety 'Fire Dragon' was an upright form of *Miscanthus* with striking orange-red foliage from the beginning of October and lasting for 4 to 5 weeks. In addition, 'Fire Dragon' bears showy, long-lasting flowers which are silver-grey in color and silky in texture. Taking these characteristics together, and after observing the consistency of the fall color of 'Fire Dragon' for more than 20 years, the inventor determined that 'Fire Dragon' would be a useful and valuable addition to the available varieties of *Miscanthus* with particular applications for mid-sized gardens, in planted containers and in landscape plantings.

Asexual propagation of 'Fire Dragon' was first accomplished by the inventor in 1998 at the inventors's garden in Woellstein, Germany. The method of propagation used was division of the entire in-ground plant. Since that time under careful observation the inventor has determined that the characteristics of 'Fire Dragon' are fixed, uniform, and true to type in all subsequent generations of asexual propagation.

SUMMARY

The following traits have been repeatedly observed and represent the distinguishing characteristics of the new *Miscanthus* cultivar 'Fire Dragon'. These traits in combination set 'Fire Dragon' apart from all other existing varieties of *Miscanthus* known to the inventor. 'Fire Dragon' has not been tested under all possible conditions and phenotypic differences may be observed with variations in environmental, climatic and cultural conditions, however, without any variance in genotype.

1. 'Fire Dragon' exhibits an upright and dense plant habit overall, with graceful arching foliage.
2. After one year's growth in a container, 'Fire Dragon' is approximately 90 cm in height and 30 cm in diameter, excluding the height of the flowers.
3. Established and mature plants of 'Fire Dragon' achieve a height of 1.5 m to 1.7 m and a spread of 60 cm at the base of the plant, and 1.5 m at maximum width of the arching foliage canopy.
4. The first spring and summer foliage growth of 'Fire Dragon' is green in color.
5. As summer proceeds into fall, the foliage of 'Fire Dragon' becomes increasingly orange-red in color, reaching its most intense color in early October, and holding that color for four to five weeks.
6. 'Fire Dragon' blooms from July to October.
7. The flowers of 'Fire Dragon' extend to a height of 60 cm to 70 cm above the foliage canopy.
8. The flowers of 'Fire Dragon' are silky in texture and silver-white in color.
9. 'Fire Dragon' is hardy in USDA Zone 5.

BRIEF DESCRIPTION OF THE PHOTOGRAPH

The accompanying color photograph illustrates the overall appearance of the new *Miscanthus* variety 'Fire Dragon' showing colors as true as it is reasonably possible to obtain in colored reproductions of this type. Colors in the photographs may differ from the color values cited in the detailed botanical description, which accurately describe the actual colors of the new variety 'Fire Dragon'.

FIG. 1 depicts an 18 year old plant of 'Fire Dragon' growing outdoors in the inventor's garden in Woellstein, Germany. This photograph was taken in October 2010 and depicts the orange-red color of the fall foliage and the silver-white color of the inflorescences.

The photograph was made using conventional techniques and although flower and foliage color may appear different from actual color due to light reflectance, they are as accurate as possible by conventional photography.

BOTANICAL DESCRIPTION OF THE PLANT

The following is a detailed botanical description of 'Fire Dragon' which has been prepared from observations and measurements of an 18 years old plant of 'Fire Dragon' growing in the ground in the inventor's garden in Woellstein, Germany. Color determinations are made in accordance with the 2007 edition of The Royal Horticultural Society Colour Chart, London, England, except where general color terms of ordinary dictionary significance are used. The growing requirements of 'Fire Dragon' are similar to the species *Miscanthus sinensis*.

Botanical classification:

*Family*.—Poaceae.
*Genus*.—*Miscanthus*.
*Species*.—*sinensis*.
*Common name*.—Maiden Grass.
*Variety*.—'Fire Dragon'.

Parentage: 'Fire Dragon' was selected as an open pollinated seedling arising from the following parents: *Miscanthus sinensis* 'Rotsilber' (unpatented), and *Miscanthus sinensis* 'Yakushima Dwarf' (unpatented).

Plant description:

*Growth habit*.—Upright, arching foliage.
*Commercial category*.—Ornamental grass.
*Use*.—For garden and landscape.
*Suitable container sizes*.—1 gallon container or larger.
*Propagation method*.—Division of established in-ground or container-grown plants; tissue culture.
*Rooting system*.—Fibrous.
*Crop time* (*range*).—9 to 12 months to produce a 1-gallon container from a plant division.
*Plant dimensions* (*first year*).—90 cm in height (excluding the flowers) and 30 cm in diameter.
*Plant dimensions* (*at maturity*).—1.5 m to 1.7 m in height (excluding the flowers), 60 cm in width at the base, and 1.5 m in width at the maximum width of the arching foliage canopy.
*Height in flower* (*including the flowers*).—1.5 m in first year, up to 2.2 m when established and mature.
*Cultural requirements*.—Grow in full sun and well-draining porous soil, with moderate water.
*Hardiness*.—USDA Zone 5.

Culm (stem):

*Dimensions*.—Up to 1.5 m in length and 0.7 cm in diameter.
*Shape*.—Cylindrical, hollow.
*Surface*.—Glabrous.
*Color*.—Emerges 146C.
*Node dimensions*.—5 mm in length, 3 mm in width.
*Internode distance*.—Averages 15 cm.
*Surface*.—Lightly pubescent.

Foliage:

*Leaves quantity*.—Up to 10 leaves per culm.
*Leaf aspect*.—Initially upright then arching and fully reflexing.
*Attachment*.—Sheathing.
*Leaf shape*.—Concave, linear.
*Leaf dimensions*.—1.0 m to 1.2 m in length, 1 cm in width (base).
*Leaf margin*.—Serrulate.
*Leaf surface* (*both surfaces*).—Glabrous.
*Leaf color* (*both surfaces, spring and summer*).—143C turning to fall color from September.
*Leaf color* (*fall, both surfaces*).—Ranges between 34A and 179A.
*Leaf apex*.—Acute.
*Leaf base*.—Truncate.
*Venation pattern*.—Parallel.
*Midrib*.—Mostly inconspicuous, color as leaf blade in all seasons. Where present, depressed on adaxial surface, raised on abaxial surface, color (both surfaces) NN155B.

Inflorescence:

*Type*.—Terminal panicle, one panicle per culm.
*Panicle appearance*.—Plumose, consisting of numerous (approximately 25) silky racemes. Racemes consist of approximately 50 spikelets arranged in pairs.
*Panicle dimensions*.—Up to 45 cm in length, 15 cm in width.
*Raceme dimensions*.—12 cm to 15 cm in length, 3 cm in width.
*Panicle and raceme color*.—Silver-white, whiter than NN155D.
*Spikelets*.—Up to 8 mm in length, 2 mm in width; fine white hairs, color silver-white, whiter than NN155D.
*Pedicel*.—5 mm in length, 1 mm in diameter, color 165B.
*Lemma dimensions*.—8 mm in length, 3 mm in diameter, color 165B. Lemma base truncate, apex acute, margin entire, texture smooth.
*Palea dimensions*.—4 mm in length, 2 mm in diameter, color 165B. Palea base truncate, apex acute, margin entire, texture smooth.
*Awn*.—1 cm in length, 0.5 mm in diameter, color 165B.
*Bloom period*.—July to October.
*Persistent or self-cleaning*.—Persistent.
*Fragrance*.—None observed.

Reproductive organs:

*Stamens*.—3 in number, filaments 2 mm to 3 mm in length, 0.2 mm in diameter, color NN155D.
*Anthers*.—2 mm in length, less than 0.5 mm in width, color 200D.
*Pistil quantity*.—1.
*Stigma*.—2 in number, shape plumose, color 200A.
*Pollen*.—Not observed.
*Ovary*.—Superior, rounded, 1 mm in diameter.

Fruit and seed: None observed to date.

Diseases and pests: None known to the inventor.

COMPARISON WITH PARENTS AND CLOSEST KNOWN VARIETY

'Fire Dragon' differs from the parent, *Miscanthus sinensis* 'Rotsilber' by color of the inflorescences. Whereas the inflorescence of 'Fire Dragon' is silver-white in color, the inflorescence of 'Rotsilber' is red-brown in color. 'Fire Dragon' differs from the parent *Miscanthus sinensis* 'Yakushima Dwarf' by plant height. The mature height of 'Fire Dragon' is approximately 50% greater than the mature height of 'Yakushima Dwarf'. In addition, both parents exhibit muted or dull fall foliage color, whereas 'Fire Dragon' exhibits striking intense orange-red foliage color.

'Fire Dragon' may also be compared with the lower-growing species *Miscanthus* 'Purpurescens' (unpatented) which also exhibits fall foliage color. The fall foliage of *Miscanthus* 'Purpurescens' is dull purple in color. In addition, the foliage of *Miscanthus* 'Purpurescens' is stiff, erect and open, whereas the foliage of 'Fire Dragon' is arching and dense.

I claim:

1. A new and distinct cultivar of *Miscanthus* plant named 'Fire Dragon' as described and illustrated herein.

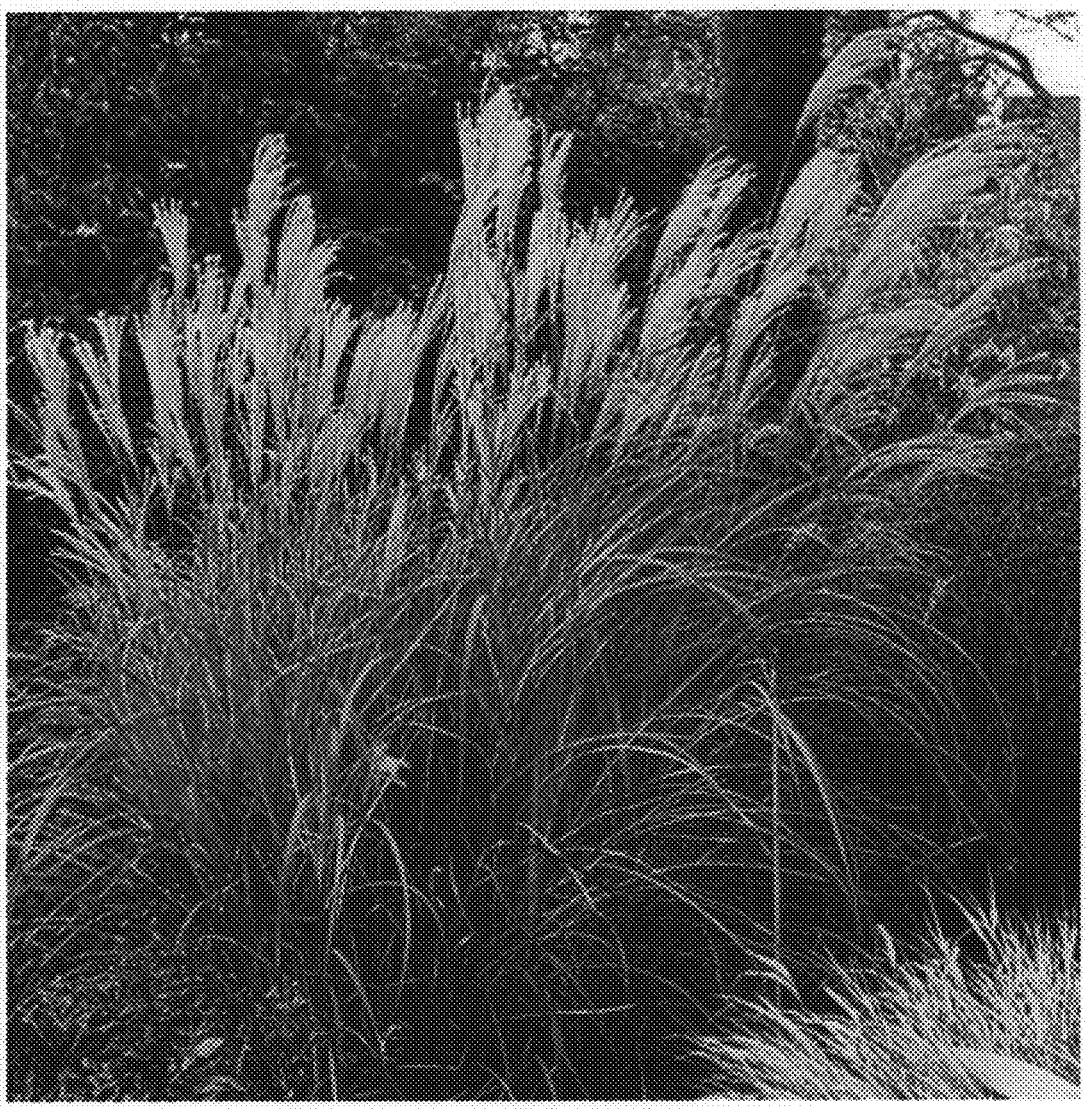

* * * * *